United States Patent [19]

Szántay et al.

[11] Patent Number: 4,474,960
[45] Date of Patent: Oct. 2, 1984

[54] APOVINCAMINIC ACID ESTERS

[75] Inventors: Csaba Szántay; Lajós Szabó; Gyorgy Kalaus; Janós Kreidl; László Czibula; Györgv Visky; Andras Nemes; Maria Farkas née Kirlyák, all of Budapest, Hungary

[73] Assignee: Richter Gedeon Vegyeszeti Gyar Rt., Budapest, Hungary

[21] Appl. No.: 387,676

[22] Filed: Jun. 11, 1982

[30] Foreign Application Priority Data

Jun. 12, 1981 [HU] Hungary ............................ 1753/81

[51] Int. Cl.³ .................. C07D 461/00; A61K 31/475
[52] U.S. Cl. ..................................................... 546/70
[58] Field of Search ......................................... 546/70

[56] References Cited
U.S. PATENT DOCUMENTS 4,316,029  2/1982  Rossey ................................. 546/70

FOREIGN PATENT DOCUMENTS 13315  7/1980  European Pat. Off. .

Primary Examiner—Paul M. Coughlan, Jr.
Assistant Examiner—D. B. Springer
Attorney, Agent, or Firm—Karl F. Ross; Herbert Dubno

[57] ABSTRACT

A process is disclosed for the preparation of racemic cis or trans apovincaminic acid esters of the formula (I)

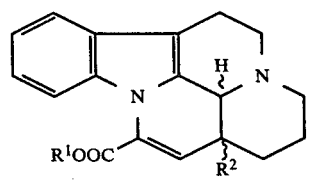

(I)

and the corresponding optically active derivatives of the formulae (Ia)

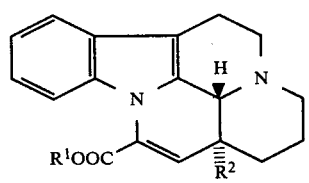

(Ia)

and/or (Ib)

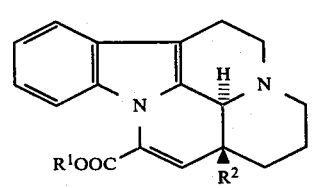

(Ib)

and/or (Ic)

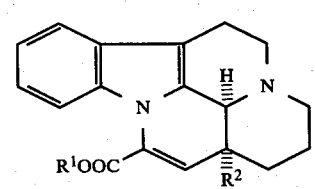

(Ic)

and/or (Id)

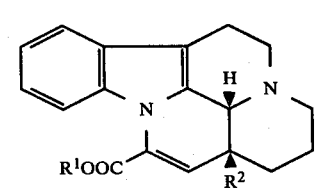

(Id)

wherein $R^1$ and $R^2$ are identical or different alkyl groups having 1 to 6 carbon atoms. Apovincaminic acid alkyl esters are well-known vasodilating compounds.

6 Claims, No Drawings

APOVINCAMINIC ACID ESTERS

The invention relates to a new process for the preparation of apovincaminic acid esters. More particularly, the invention concerns a new process for preparing racemic cis and/or trans apovincaminic acid esters of the formula (I)

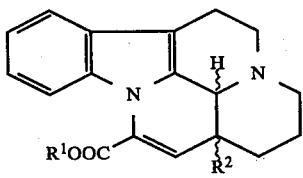

(I)

and the corresponding optically active derivatives of the formulae (Ia)

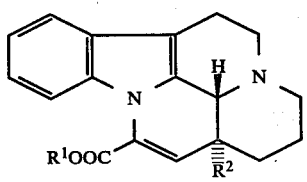

(Ia)

and/or (Ib)

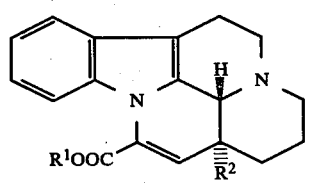

(Ib)

and/or (Ic)

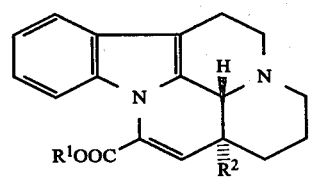

(Ic)

and/or (Id)

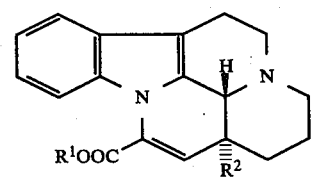

(Id)

In the above formulae $R^1$ and $R^2$ are identical or different alkyl groups having from one to 6 carbon atoms.

According to the invention racemic cis and/or trans compounds of the formula (I) and the corresponding optically active compounds of the formulae (Ia) and/or (Ib) and/or (Ic) and/or (Id) are prepared by a synthesis in which if desired, racemic hexahydroindolo[2,3-a]–quinolizinium derivatives of the formula (V)

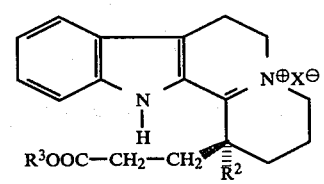

(V)

wherein
$R^2$ and $R^3$ are identical or different alkyl groups having from one to 6 carbon atoms, and
X stands for an acid residue or an alkanolate having from one to 6 carbon atoms,
are resolved with optically active dibenzoyltartaric acid, and optically active hexahydroindolo[2,3-a]quinolizinium derivatives of the formula (Va)

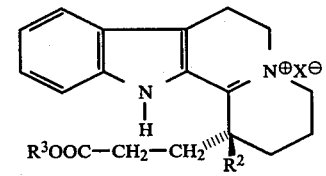

(Va)

and/or (Vb)

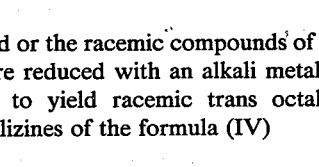

(Vb)

obtained or the racemic compounds of the formula (V), (a) are reduced with an alkali metal hydride, if it is desired to yield racemic trans octahydroindolo[2,3-a]quinolizines of the formula (IV)

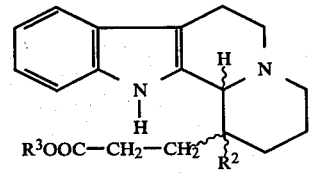

(IV)

which are resolved with D-tartaric acid and from the optically active tartarates obtained the corresponding optically active bases are set free, and the optically active octahydroindolo[2,3-a]quinolizine derivatives of the formulae (IVa)

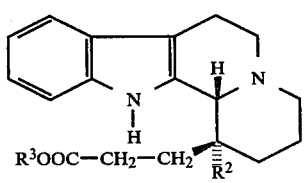

(IVa)

and/or (IVb)

-continued

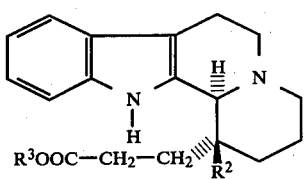
(IVb)

or the racemic trans octahydroindolo[2,3-a]quinolizines of the formula (IV), if desired, are subjected to alkaline hydrolysis, and the racemic trans octahydroindolo[2,3-a]quinolizinecarboxylic acids of the formula (III)

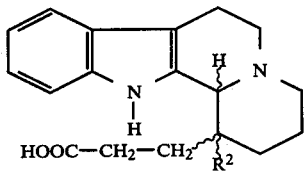
(III)

or the corresponding optically active derivatives of the formulae (IIIa)

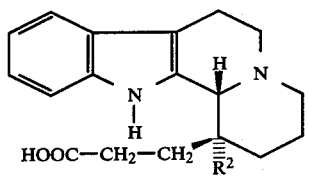
(IIIa)

and/or (IIIb)

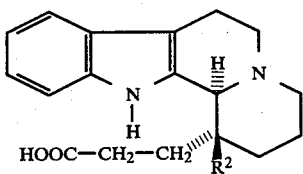
(IIIb)

if desired after resolving racemic trans compounds of the formula (III), are esterified, and the optically active octahydroindolo[2,3-a]quinolizine derivatives of the formulae (VIa)

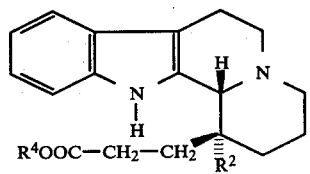
(VIa)

and/or (VIb)

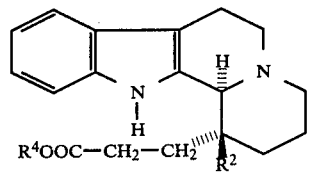
(VIb)

obtained or the corresponding racemic trans compounds of the formula (VI)

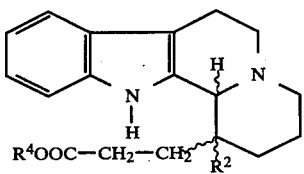
(VI)

wherein $R^4$ is an alkyl group having from one to 6 carbon atoms, which may be identical with or different from $R^3$, are treated with tert.-butyl nitrite in an aromatic hydrocarbon solvent, subsequently with an alkali metal tert.-alcoholate and optionally with an aprotic dipolar solvent and if desired, with an alkanol of the formula $R^5$—OH, wherein $R^5$ is an alkyl group having from one to 6 carbon atoms, which may be identical with or different from $R^4$, the racemic trans hydroxyiminooctahydroindolo[2,3-a]-quinolizine derivatives of the formula (II)

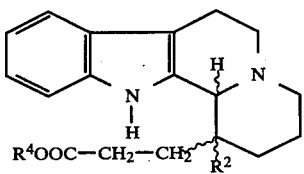
(II)

or the corresponding optically active derivatives of the formulae (IIa)

(IIa)

and/or (IIb)

(IIb)

wherein $R^2$ has the same meaning as defined above and $R^1$ is identical with $R^4$ or $R^5$, if desired after converting them into their acid addition salts and/or resolving the racemic trans compounds of the formula (II), are treated with a concentrated, not volatile acid, in an inert organic solvent, to yield racemic trans compounds of the formula (I) or the optically active compounds of the formulae (Ia) and/or (Ib); or (b) are subjected to catalytic hydrogenation, if desired the racemic cis octahydroindolo[2,3-a]quinolizines of the formula (IV)

(IV)

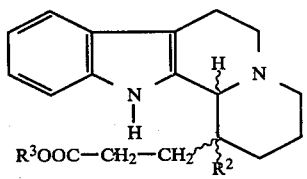

are resolved with D-tartaric acid and from the optically active tartarates obtained the corresponding optically active bases are set free, and the optically active octahydroindolo[2,3-a]quinolizine derivatives of the formulae (IVc)

(IVc)

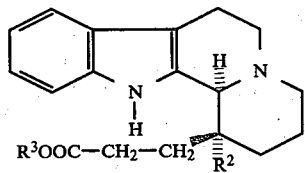

and/or (IVd)

(IVd)

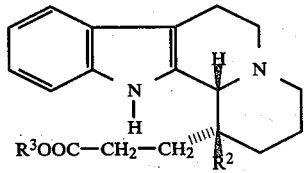

or the racemic cis octahydroindolo[2,3-a]quinolizines of the formula (IV), if desired, are subjected to alkaline hydrolysis, and the racemic cis octahydroindolo[2,3-a]quinolizinecarboxylic acids of the formula (III)

(III)

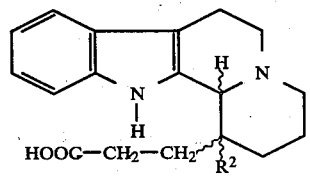

or the corresponding optically active derivatives of the formulae (IIIc)

(IIIc)

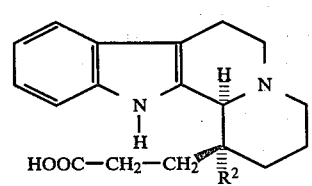

and/or (IIId)

(IIId)

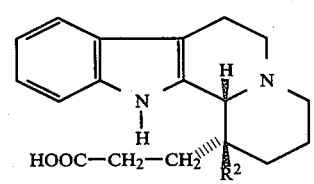

wherein $R^2$ has the same meaning as defined above, if desired after resolving racemic cis compounds of the formula (III), are esterified, and the optically active octahydroindolo[2,3-a]quinolizine derivatives of the formulae (VIc)

(VIc)

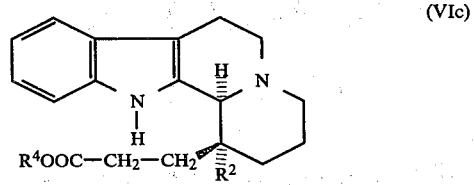

and/or (VId)

(VId)

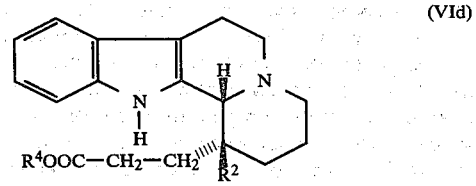

obtained or the corresponding racemic cis compounds of the formula (VI)

(VI)

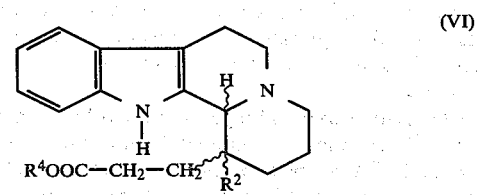

wherein $R^4$ is an alkyl group having from one to 6 carbon atoms, which may be identical with or different from $R^3$, are treated with tert.-butyl nitrite in an aromatic hydrocarbon solvent, subsequently with an alkali metal tert.-alcoholate and optionally with an aprotic dipolar solvent and if desired, with an alkanol of the formula $R^5$—OH, wherein $R^5$ is an alkyl group having from one to 6 carbon atoms, which may be identical with or different from $R^4$, the racemic cis hydroxyiminooctahydroindolo[2,3-a]quinolizine derivatives of the formula (II)

(II)

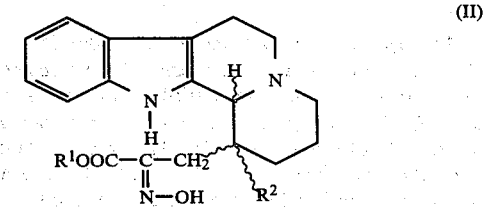

or the corresponding optically active derivatives of the formulae (IIc)

(IIc)

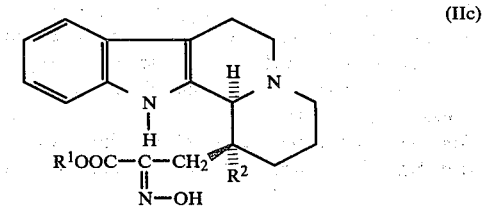

-continued and/or (IId)

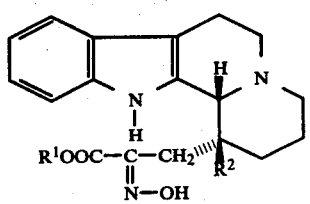

(IId)

wherein $R^1$ is identical with $R^4$ or $R^5$, if desired after converting them into their acid addition salts and/or resolving the racemic cis compounds of the formula (II), are treated with a concentrated, not volatile acid, in an inert organic solvent, to yield racemic cis compounds of the formula (I) or the optically active compounds of the formulae (Ic) and/or (Id) and if desired, racemic cis or trans compounds of the formula (I) or the optically active trans compounds of the formulae (Ia) and/or (Ib) or the optically active cis compounds of the formulae (Ic) and/or (Id) are transesterified in a manner known per se.

It is well known that racemic cis apovincaminic acid esters of the formula (I) and the optically active cis compounds of the formula (Ic) possess valuable pharmaceutical properties, and in particular (+)-cis-apovincaminic acid ethyl ester shows excellent vasodilating activity.

According to the Hungarian Patent Specification No. 163,143 racemic, cis compounds of the formula (I) and optically active, cis compound of the formula (Ic) were prepared by hydrolyzing the pharmaceutically active vincamine and converting the vincaminic acid obtained into a desired ester from which the corresponding apovincaminic acid ester was obtained by splitting off water; or alternatively, vincamine was first converted into apovincamine by splitting off water which was then subjected to hydrolysis and the apovincaminic acid obtained was converted into a desired ester. This process is disadvantageous in that at first vincamine should be prepared by a multi-step synthesis from which the corresponding apovincaminic acid esters can be prepared with a yield of at most 60% only.

Racemic, trans compounds of the formula (I) were described in the European Patent Application No. 13315.

The optically active trans compounds of the formulae (Ia) and (Ib) prepared according to the invention are new and show valuable antiinflammatory, anticonvulsive, CNS, anticholinergic, antiparkinsonism and antiatherosclerotic activities. The last intermediates of the formulae (II), (IIa), (IIb), (IIc) and (IId) are also new and may be utilized in treating cardiovascular diseases. The optically active intermediates of the formulae (IIIa), (IIIb), (IIIc) and (IIId), have antihypoxic and anticonvulsive activities, and the optically active intermediates of the formulae (IVa), (IVb), (IVc), (IVd) and (VIa), (VIb), (VIc), (VId), respectively show antiallergic, antibradykinine, CNS, antiarrhythmic antihypoxic, anticonvulsive, antidepressive, sedative, hypnotic, cholesterine, antiallergic and antiulcer activities and decrease the lipoprotein level. These compounds have first been described in the Hungarian Patent Application No. 171 660 and some of them are patent vasodilators.

Moreover, all intermediates according to the invention are valuable starting compounds for other pharmaceutically active compounds having an indoloquinolizine or eburnane skeleton, e.g. vincamine, vincamone, etc.

The invention includes all processes for the preparation of compounds of the formulae (I), (Ia), (Ib), (Ic) and (Id), starting from compounds of the formulae (V), (Va), (Vb) or (IV), (IVa), (IVb), (IVc) or (IVd) or (VI), (VIa), (VIb), (VIc) or (VId) or (III), (IIIa), (IIIb), (IIIc), (IIId) or (II), (IIa), (IIb), (IIc) or (IId).

The invention further relates to the preparation of all new intermediates, i.e. compounds of the formulae (II), (IIa), (IIb), (IIc) and (IId), In other words, the process according to the invention may be interrupted at any stage of the synthesis, i.e. at any intermediate or may be accomplished starting from any intermediate.

In the formulae in the symbols $R^1$, $R^2$, $R^3$, $R^4$ and $R^5$ the alkyl groups having from one to 6 carbon atoms may be straight or branched chained alkyls having from one to 6 carbon atoms, i.e. methyl, ethyl, n-propyl, isopropyl, n-butyl, sec.-butyl, tert.-butyl, n-pentyl, isopentyl, n-hexyl or isohexyl groups.

X as an acid residue may represent a residue of any organic or inorganic acid and preferably is a perhalogenate, e.g. perchlorate; and as an alkanolate stands for an alkanolate corresponding to any of the alkyls referred to in connection with $R^1$, $R^2$, $R^3$, $R^4$ and $R^5$, preferably methanolate.

Resolution of the racemic cis and racemic trans compounds of the formulae (IV) and (V) is carried out in any organic solvent or solvent mixture inert under the reaction conditions. Suitable solvents include e.g. aliphatic or aromatic hydrocarbons optically substituted by one or more halogens, such as dichloromethane; or alkanols having from one to 6 carbon atoms, such as methanol, ethanol or mixtures thereof.

For catalytic hydrogenation of the compounds of formulae (V), (Va) and (Vb) as a catalyst preferably palladium-on-charcoal is employed but the reaction may be successfully performed in the presence of any conventional hydrogenation metal catalyst, optionally precipitated on a carrier, as well. Catalytic hydrogenation is carried out in the presence of an organic solvent or solvent mixture inert under the reaction conditions. Suitable solvents include aprotic dipolar solvents, such as dimethyl formamide; or protic solvents, such as alkanols having from one to 6 carbon atoms, such as methanol, ethanol, etc. or mixtures thereof.

The reduction of the compounds of the formulae (V), (Va) and (Vb) is preferably carried out in the presence of sodium borohydride but for example lithiumaluminum hydride may also be employed. The reduction is carried out in an alkanol having from one to 6 carbon atoms, such as methanol, ethanol, etc.

The alkaline hydrolysis of the compounds of the formulae (IV), (IVa), (IVb) and (IVc), (IVd) is performed in a mixture of an inorganic base, e.g. alkali metal hydride, such as sodium hydride, an alkanol having from one to 6 carbon atoms and water.

The acids of the formulae (III), (IIIa), (IIIb), (IIIc) and (IIId) obtained by alkaline hydrolysis may be converted into a corresponding salt by a suitable base, or into other functional derivatives, e.g. acid halides, acid amides, nitriles, acid anhydrides, acid azides, etc.

Esterification of the compounds of the formulae (III), (IIIa), (IIIb), (IIIc) and (IIId) may be carried out by any of the known methods.

When converting compounds of the formulae (VI), (VIa), (VIb), (VIc), and (VId) into compounds of the formulae (II), (IIa), (IIb), (IIc), and (IId), respectively, as an aromatic hydrocarbon solvent for example benzene, toluene, xylene, etc. may be employed. Suitable alkali metal tertiary alcoholates include potassium or sodium alcoholates having 4 to 8 carbon atoms, e.g. potassium tert.-butylate, sodium-tert.-butylate, potassium tert.-amylate, sodium tert.-amylate. Optionally an aprotic dipolar solvent, e.g. dimethyl formamide, dimethyl acetamide, etc. may also be added to the reaction mixture just as an alkanol of the formula $R^5$—OH.

Compounds of the formulae (II), (IIa), (IIb), (IIc) and (IId) are then treated with a concentrated nonvolatile acid, for example a concentrated mineral acid e.g. concentrated sulfuric acid; or an organic aliphatic or aromatic sulfonic acid, such as methanesulfonic acid, ethanesulfonic acid, dodecylsulfonic acid, benzenesulfonic acid, p-toluene-sulfonic acid, α-naphthylsulfonic acid, β-naphthylsulfonic acid, etc. The acid treatment may be accomplished in an inert organic solvent, e.g. an alkanol having from one to 6 carbon atoms, such as methanol, ethanol, etc.; or in an aprotic organic solvent, e.g. an aromatic hydrocarbon optionally substituted with one or more halogene, such as benzene, toluene, xylene, chlorobenzene; or in cyclic ethers, such as dioxane.

The invention will now be illustrated in greater detail in the following Examples, which are given for illustration and not limitation of our invention.

EXAMPLE 1

Resolution of 1-(methoxycarbonylethyl)-1-ethyl-1,2,3,4,6,7-hexahydro-12H-indolo[2,3-a]quinolizinium methanolate 100.0 g. (0.2699 moles) of 1-(2′-methoxycarbonylethyl)-1-ethyl-1,2,3,4,6,7-hexahydro-12H-indolo[2,3-a]quinolizinium methanolate are dissolved in 200.0 ml. of dichloromethane at room temperature, whereupon a solution of 100.0 g. of dibenzoyl-1-tartaric acid monohydrate (0.2673 moles) in 400.0 ml. of dichloromethane is added with stirring. The mixture is stirred at room temperature for one hour, whereupon the precipitated substance is filtered off, washed with dichloromethane and dried. 91.84 g. (0.1322 moles) of 1β-(2′-methoxycarbonyl-ethyl)-α-ethyl-1,2,3,4,6,7-hexahydro-12H-indolo[2,3-a]quinolizinium-dibenzoyl tartarate are obtained. Yield: 98.0% (calculated for the α-ethyl form).

$a_D^{20} = -68.6°$ (c = 1, in DMF).

Base content: 48.49% (theoretical: 48.73%).

Melting point: 139.5° to 140° C.

From the salt obtained the corresponding base is set free, which is then converted into the corresponding methanolate and perchlorate, respectively.

1β-(2′-methoxycarbonylethyl)-1α-ethyl-1,2,3,4,6,7-hexahydro-12H-indolo[2,3-a]quinolizinium methanolate: melting point: 151° to 152° C.

$[a_D^{20}] = -27.6°$ (c = 1, DMF).

1β-(2′-methoxycarbonylethyl)-1α-ethyl-1,2,3,4,6,7-hexahydro-12H-indolo[2,3-a]quinolizinium $HClO_4$: melting point: 178° to 180° C.

$[a_D^{20}] = -23.5°$ (c = 1, DMF).

From the mother liquor of the resolution the corresponding salts of the β-ethyl antipode may be prepared, after setting free the base.

EXAMPLE 2

The resolution of 1-(methoxycarbonylethyl)-1-ethyl-1,2,3,4,6,7-hexahydro-12H-indolo[2,3-a]quinolizinium methanolate 100.0 g. (0.2699 moles) of 1-(2′-methoxycarbonylethyl)-1-ethyl-1,2,3,4,6,7-hexahydro-12H-indolo[2,3-a]quinolizinium methanolate are dissolved in 200.0 ml. of dichloromethane at room temperature, whereupon a solution of 100.0 g. (0.2673 moles) of dibenzoyl-d-tartaric acid in 400.0 ml. of dichloromethane is added. After stirring at room temperature for one hour the reaction mixture is filtered, washed with dichloromethane and dried.

91.7 g. (0.1320 moles) of 1-1α(methoxycarbonylethyl)-1β-ethyl-1,2,3,4,6,7-hexahydro-12H-indolo[2,3-a]quinolizinium dibenzoyl tartarate are obtained. Yield: 97.8%. (calculated for the 1β-ethyl antipode).

$[a_D^{20}] = +68.8°$ (c = 1, DMF).

Base content: 48.5% (theoretical: 48.73%).

Melting point: 139° to 140° C.

From the crude compound obtained the corresponding methanolate and perchlorate salts can be prepared, after setting free the corresponding base.

1α-(methoxycarbonylethyl)-1β-ethyl-1,2,3,4,6,7-hexahydro-12H-indolo[2,3-a]quinolizinium methanolate: melting point: 150° to 152° C.

$[a_D^{20}] = +27.8°$ (c = 1, DMF).

1α-(methoxycarbonylethyl)1β-ethyl-1,2,3,4,6,7-hexahydro-12H-indolo[2,3-a]quinolizinium perchlorate: melting point: 178.5° to 180° C.

$[a_D^{20}] = +24°$ (c = 1, DMF).

From the mother liquor of the resolution the corresponding salts of the α-ethyl antipode can also be prepared, after setting free the base.

EXAMPLE 3

(−)-1β-(2′-Methoxycarbonylethyl)-1α-ethyl-1,2,3,4,6,7,12,12b α-octahydro-indolo[2,3-a]quinolizine 34.7 g (0.05 moles) of (−)-1β-(2′-methoxycarbonylethyl)-1β-ethyl-1,2,3,4,6,7-hexahydro-12H-indolo[2,3-a]quinolizine-5-ium (−)-dibenzoyltartarate in 70 ml. of dimethyl formamide, in the presence of 0.25 g. of a 10% palladium-on-charcoal catalyst are hydrogenated for 2.5 hours, at 40° C., under atmospheric pressure.

Catalyst is filtered off and is then washed with altogether 10 ml. of dimethyl formamide in two portions. To the filtrate 200 ml. of a 5% aqueous methanol solution is poured under vigorous stirring. The (−)-dibenzoyl tartarate of the title compound is precipitated. The product is washed with altogether 10 ml. of cold methyl alcohol in two portions and dried.

Yield: 26 g. (75%).

Melting point: 150°–152° C.

$[a_D^{20}] = -120.1°$ (c = 2, DMF).

EXAMPLE 4

(+)-1α-(2′-Methoxycarbonylethyl)-1β-ethyl-1,2,3,4,6,7,12,12bβ-octahydro-indolo[2,3-a]quinolizine Following the procedure described in Example 3 but starting from 34.7 g. (0.05 moles) of (+)-1α-(2′-methoxycarbonyl-ethyl)-1β-1,2,3,4,6,7-hexahydro-12H-indolo[2,3-a]quinolizine-5-ium (+)-dibenzoyltartarate, the title compound is obtained, weighing 25.5 g (73.5%).

Melting point: 150° to 151° C.
$[\alpha_D^{20}] = +119.8°$ (c=2, DMF).

EXAMPLE 5

(+)-1β-(2'-Methoxycarbonylethyl)-1α-ethyl-1,2,3,4,6,7,12,12bβ-octahydro-indolo[2,3-a]quinolizine 4.39 g. (0.01 moles) of (−)-1β-(2'-methoxycarbonylethyl)-1α-ethyl-1,2,3,4,6,7-hexahydro-12H-indolo[2,3-a]quinolizine-5-ium perchlorate are suspended in 100 ml. of methyl alcohol at 60° C., and at the same temperature 1.2 g. of sodium borohydride are added in one hour, in more portions, whereupon the mixture is stirred for an additional one hour. 70 ml. of methyl alcohol are distilled off from the reaction mixture, the residue is stirred at 0° C., washed by covering with cold methyl alcohol and washed to neutral with distilled water. 1.7 g. (50%) of the title compound are obtained, melting at 108° to 109° C.
$[\alpha_D^{20}] = +69.7°$ (c=1, CHCl$_3$).

EXAMPLE 6

(−)-1α(2'-Methoxycarbonylethyl)-1β-ethyl-1,2,3,4,6,7,12,12bα-octahydro-indolo[2,3-a]quinolizine Following the procedure described in Example 5 but starting from 4.39 g. (0.01 moles) of (+)-1α-(2'-methoxycarbonylethyl)-1β-ethyl-1,2,3,4,6,7-hexahydro-12H-indolo[2,3-a]quinolizin-5-ium perchlorate, 1,73 g. (51%) of the title compound are obtained, melting at 108° to 109° C.
$[\alpha_D^{20}] = -68.9°$ (c=1, CHCl$_3$).

EXAMPLE 7

Resolution of racemic trans 1-(2'-methoxycarbonylethyl)-1-ethyl-1,2,3,4,6,7,12,12b-octahydro-indolo[2,3-a]quinolizine 34 g. (0.1 moles) of the title compound are suspended in 400 ml. of methyl alcohol at 55° C. and a solution of 15 g. (0.1 moles) of D-tartaric acid in 40 ml. of methyl alcohol of 55° C. is added at the same temperature. The homogeneous solution is cooled to 15° C. The precipitated (+)-1β-(2'-methoxycarbonylethyl)-1α-ethyl-1,2,3,4,6,7,12,12bβ-octahydro-indolo[2,3-a]quinolizin-5-ium D-tartarate is filtered and washed with altogether 50 ml. of cold methanol in two portions. 24.1 g. (98.3%) of the above compound are obtained, melting at 213° to 215° C. $[\alpha_D^{20}] = +44.8°$ (c=1, DMF)

The corresponding base is set free as follows:

The product is dissolved in 200 ml. of water, the pH is adjusted to 9 with aqueous ammonia and the mixture is extracted with altogether 120 ml. of dichloromethane, in three portions. After drying the solution is evaporated and the obtained oily residue is boiled with 30 ml. of methanol. 15.5 g. (91.5%) of (+)-1β-(2'-methoxycarbonylethyl)-1α-ethyl-1,2,3,4,6,7,12,12bβ-octahydro-indolo[2,3-a]quinolizine are obtained, melting at 108.5° to 109° C.
$[\alpha_D^{20}] = +70.1°$ (c=1, CHCl$_3$).

From the methanolic mother liquor of the resolution the other optically active isomer is isolated. It is evaporated to 100 ml., diluted with 200 ml. of water and after adjusting the pH to 9 by aqueous ammonia and is extracted with altogether 120 ml. of dichloromethane in three portions. The mixture is dried, evaporated and the oily residue is boiled with 30 ml. of methanol. 15.1 g. (89%) of (−)-1α-(2'-methoxycarbonylethyl)-1β-ethyl-1,2,3,4,6,7,12,12bβ-octahydro-indolo[2,3-a]quinolizine are obtained, melting at 109° C.
$[\alpha_D^{20}] = -69.4°$ (c=1, CHCl$_3$).

EXAMPLE 8

(+)-1β-(2'-Carboxyethyl)-1α-ethyl-1,2,3,4,6,7,12,12bβ-octahydro-indolo[2,3-a]quinolizine 6.8 g. (0.02 moles) of (+)-1β-(2'-methoxycarbonylethyl)-1α-ethyl-1,2,3,4,6,7,12,12bβ-octahydro-indolo[2,3-a]quinolizine, 80 ml. of methanol, 4 ml. of water and 2 g. of sodium hydroxide are refluxed for one hour, whereupon 50 ml. of the mixture are distilled off under reduced pressure, 80 ml. of water are added and the pH is adjusted to 6.5 with a 1M aqueous citric acid solution, at 60° C. The title compound is filtered off at 20° C. and is then washed with altogether 50 ml. of distilled water in two portions. 6.34 g. (99%) of the title compound are obtained, melting at 144° C. with decomposition.
$[\alpha_D^{20}] = +52.4°$ (c=1, ethanol).

EXAMPLE 9

(−)-1α-(2'-Carboxyethyl)-1β-ethyl-1,2,3,4,6,7,12,12bα-octahydro-indolo[2,3-a]quinolizine Following the procedure described in Example 8 but starting from 6.8 g. (0.2 moles) of (−)-1α-(2'-methoxycarbonylethyl)-1β-ethyl-1,2,3,4,6,7,12,12bα-octahydro-indolo[2,3-a]quinolizine are obtained, melting at 144° C. with decomposition.
$[\alpha_D^{20}] = -48.6°$ (c=1, ethanol).

EXAMPLE 10

(−)-1β-[(2'-Methoxycarbonyl-2'-hydroxyimino)-ethyl]-1α-ethyl-1,2,3,4,6,7,12,12bα-octahydro-indolo[2,3,-a]quinolizine and its hydrochloride To 34 g. (0.1 moles) of (−)-1β-(2'-methoxycarbonylethyl)-1α-ethyl-1,2,3,4,6,7,12,12bα-octahydro-indolo[2,3-a]quinolizine 20 ml. of absolute toluene, a 55 to 60% toluene solution of 30 ml. of tert.-butyl nitrite and then 17 g. (0.15 moles) of potassium tert.-butylate are added. The mixture is stirred at 25° to 30° C. for 20 minutes, 150 ml. of absolute methanol are slowly added and the mixture is stirred at 40° C. for 3 hours. The reaction mixture is then cooled to 20° C., is acidified up to pH=1 with concentrated hydrochloric acid, 50 ml. of water are added and the mixture is stirred at +5° C. for 2 hours. The precipitate is filtered off, the KCl is washed out with water and the precipitate is dried. 32.5 g. (80%) of hydrochloride of the title compound are obtained, melting at 265° to 272° C. with decomposition.
$[\alpha_D^{20}] = -57°$ (c=1, DMF).

From the hydrochloride obtained the free base is prepared by suspending the salt in 80 ml. of methanol and adding a mixture of 25 ml. of 25% aqueous ammonium hydroxide solution and 40 ml. of water dropwise, with stirring. After one hour stirring it is cooled to 10° C., filtered, washed with water and dried, 24 to 25 g. of the title compound are obtained, melting at 208° to 210° C.
$[\alpha_D^{20}] = -62°$ (c=1, DMF).

EXAMPLE 11

(−)-1β-[(2′-Methoxycarbonyl-2′-hydroxyimino)-ethyl]-1α-ethyl-1,2,3,4,6,7,12,12bα-octahydro-indolo[2,3-a]quinolizine (a) Following the procedure described in Example 10 but replacing K-tert.-butylate by 15 g. of Na-tert.-butylate 24 g. (60%) of the title compound are obtained.

(b) Following the procedure under point (a) but adding also 7 ml. of dimethyl formamide to the reaction mixture, 32.5 g (80%) of the title compound are obtained.

EXAMPLE 12

(−)-1β-[(2′-Ethoxycarbonyl-2′-hydroxyimino)-ethyl]-1α-ethyl-1,2,3,4,6,7,12,12bα-octahydro-indolo[2,3-a]quinolizine and its hydrochloride Following the procedure described in Example 10 but replacing methanol by 150 ml. of absolute ethanol, 25 g. of the HCl salt of the title compound (60%) are obtained, melting at 257° to 260° C.

$[\alpha_D^{20}] = -55°$ (c=1, DMF).

The corresponding base is set free in aqueous ethanol with a 25% ammonium hydroxide solution, according to Example 10. 21 g. of the title compound are obtained, melting at 172° to 173° C.

$[\alpha_D^{20}] = -118°$ (c=1, CHCl$_3$).

EXAMPLE 13

(+)-1α-[(2′-Ethoxycarbonyl-2′-hydroxyimino)-ethyl]-1β-ethyl-1,2,3,4,6,7,12,12bβ-octahydro-indolo[2,3-a]quinolizine and its hydrochloride Following the procedure described in Example 10 but starting from 34 g. of (+)-1α-(2′-methoxycarbonylethyl)-1β-ethyl-1,2,3,4,6,7,12,12bβ-octahydro-indolo[2,3-a]quinolizine and using 150 ml. of absolute ethanol as an alcohol, 25.2 g. (60%) of the hydrochloride of the title compound are obtained, melting at 258° to 260° C.

$[\alpha_D^{20}] = +55°$ (c=1, DMF).

The corresponding base is set free in aqueous ethanol with a 25% ammonium hydroxide solution, according to Example 10. 21.3 g. of the title compound are obtained, melting at 171° to 172° C.

$[\alpha_D^{20}] = +118°$ (c=1, CHCl$_3$)

EXAMPLE 14

(−)-1α-[(2′-Methoxycarbonyl-2′-hydroxyimino)-ethyl]-1β-ethyl-1,2,3,4,6,7,12,12bα-octahydro-indolo[2,3-a]quinolizine and its hydrochloride Following the procedure described in Example 10 but starting from 34 g. (0.1 moles) of (−)-1α-(2′-methoxycarbonylethyl)-1β-ethyl-1,2,3,4,6,7,12,12bβ-octahydro-indolo[2,3,-a]quinolizine, 24.3 g. (60%) of the hydrochloride of the title compound are obtained, melting at 214° to 215° C.

$[\alpha_D^{20}] = -46°$ (c=1, DMF).

The hydrochloride obtained is suspended in 50 ml. of water, 100 ml. of chloroform are added, whereupon the pH is adjusted to 9 with a 25% aqueous ammonium hydroxide solution. The chloroform phase is separated, the aqueous phase is extracted with 20 ml. of chloroform. The combined organic phase is dried over sodium sulfate, evaporated in vacuo and the residue is recrystallized from 30 ml. of dichloroethane. 16 g. of the title compound are obtained, melting at 166° to 168° C.

$[\alpha_D^{20}] = -54°$ (c=1, DMF).

EXAMPLE 15

(+)-1β-[(2′-Methoxycarbonyl-2′-hydroxyimino)-ethyl]-1α-ethyl-1,2,3,4,6,7,12,12bβ-octahydro-indolo[2,3-a]quinolizine and its hydrochloride Following the procedure described in Example 10 but starting from 34 g. (0.1 moles) of (+)-1β-(2′-methoxycarbonylethyl)-1α-ethyl-1,2,3,4,6,7,12,12bβ-octahydro-indolo[2,3-a]quinolizine, 25 g. (61.5% ) of the hydrochloride of the title compound are obtained, melting at 214° at 215° C.

$[\alpha_D^{20}] = +46°$ (c=1, DMF).

From the hydrochloride the corresponding free base is obtained, as described in Example 14. 19.2 g. of the title compound are obtained, melting at 166° to 168° C.

$[\alpha_D^{20}] = +53.2°$ (c=1, DMF).

EXAMPLE 16

(−)-1α-[(2′-Ethoxycarbonyl-2′-hydroxyimino)-ethyl]-1β-ethyl-1,2,3,4,6,7,12,12bα-octahydro-indolo[2,3-a]quinolizine hydrochloride Following the procedure described in Example 10 but starting from 35.4 g. (0.1 moles) of (−)-1α-(2′-ethoxycarbonylethyl)-1β-ethyl-1,2,3,4,6,7,12,12bα-octahydro-indolo[2,3,-a]quinolizine and using 150 ml. of absolute ethanol as an alcohol, 23 g. (55%) of the title compound are obtained, melting at 247° to 249° C.

$[\alpha_D^{20}] = -44°$ (c=1, DMF).

EXAMPLE 17

(+)-1β-[(2′-Ethoxycarbonyl-2′-hydroxyimino)-ethyl]-(1α-ethyl-1,2,3,4,6,7,12,12bβ-octahydro-indolo[2,3-a]quinolizine hydrochloride Following the procedure described in Example 10 but starting from 35.4 g. (0.1 moles) of (+)-1β-(2′-ethoxycarbonylethyl)-1α-ethyl-1,2,3,4,6,7,12,12bβ-octahydro-indolo[2,3-a]quinolizine and using 150 ml. of absolute ethanol as an alcohol, 23.2 g. of the title compound are obtained, melting at 248° to 249° C.

$[\alpha_D^{20}] = +45°$ (c=1, DMF).

EXAMPLE 18

Racemic trans 1-[(2′-Ethoxycarbonyl-2′-hydroxyimino)-ethyl]-1ethyl-1,2,3,4,6,7,12,12b-octahydro-indolo[2,3-a]quinolizine hydrochloride Following the procedure described in Example 10 but starting from 35.4 g. (0.1 moles) of racemic trans 1-(ethoxycarbonylethyl)-1-ethyl-1,2,3,4,6,7,12,12b-octahydro-indolo[2,3-a]quinolizine and using 150 ml. of absolute ethanol as an alcohol, 25.1 g. (60%) of the title compound are obtained, melting at 226° to 228° C. (decomp.).

$[\alpha_D^{20}] = \pm 0$ (c=1, DMF).

EXAMPLE 19

(+)-Trans apovincaminic acid ethylester 4.75 g. (0.025 moles) of p-toluenesulfonic acid monohydrate are refluxed in a flask equipped with a Marcusson water condenser, under atmospheric pressure, whereupon the toluene is made up to 70 ml. and 4.2 g. (0.01 moles) of (−)-1α-[(2′-ethoxycarbonyl-2′-hydroxyimino)-ethyl]-1β-ethyl-1,2,3,4,6,7,12,12bα-octahydro-indolo[2,3-a]quinolizine hydrochloride are added. The reaction mixture is refluxed for 1.5 hours and 30 ml. of water are added at room temperature. The mixture is adjusted to pH 9 with an aqueous ammonia solution. After separation the toluene phase is evaporated under reduced pressure, the oily residue is boiled with 5 ml. of ethanol and filtered at 0° C. 3.14 g. (90%) of the title compound are obtained, melting at 120° to 122° C.

$[\alpha_D^{20}] = +144.4°$ (c=1, CHCl$_3$).

EXAMPLE 20

(−)-Trans-apovincaminic acid ethylester

Following the procedure according to Example 19 but starting from 4.2 g. (0.01 moles) of (+)-13-[(2'-ethoxycarbonyl-2'-hydroxyimino)-ethyl]-1α-ethyl-1,2,3,4,6,7,12,12bβ-octahydro-indolo[2,3-a]quinolizine hydrochloride, 3.18 g. (91%) of the title compound are obtained, melting at 121° to 122° C.

$[\alpha_D^{20}] = -147.6°$ (c=1, CHCl$_3$).

EXAMPLE 21

Racemic trans-apovincaminic acid ethylester

Following the procedure according to Example 19 but starting from 4.2 g. (0.01 moles) of racemic trans 1-[(2'-ethoxycarbonyl-2'-hydroxyimino)-ethyl]-1-ethyl-1,2,3,4,6,7,12,12b-octahydro-indolo[2,3-a]quinolizine hydrochloride (Example 21), 3.22 g. (92%) of the title compound are obtained, melting at 106° to 108° C.

$[\alpha_D^{20}] = \pm 0$ (c=1, CHCl$_3$).

EXAMPLE 22

Racemic cis-apovincaminic acid ethylester

Following the procedure described in Example 19 but starting from 4.2 g. (0.01 moles) of racemic cis 1-[(2'-ethoxycarbonyl-2'-hydroxyimino)-ethyl]-1-ethyl-1,2,3,4,6,7,12,12b-octahydro-indolo[2,3-a]quinolizine hydrochloride, 3.22 g. (92%) of the title compound are obtained, melting at 122° C.

$[\alpha_D^{20}] = \pm 0$ (c=1, CHCl$_3$).

EXAMPLE 23

(+)-cis-apovincaminic acid ethylester

Following the procedure described in Example 19 but starting from 4.2 g (0.01 moles) of (−)-1α-[(2'-ethoxycarbonyl-2'-hydroxyimino)-ethyl]-1α-ethyl-1,2,3,4,6,7,12,12bα-octahydro-indolo[2,3-a]quinolizine hydrochloride, 3.14 g. (90%) of the title compound are obtained, melting at 148° to 151° C.

$[\alpha_D^{20}] = +147°$ (c=1, CHCl$_3$).

EXAMPLE 24

(−)-cis-apovincaminic acid ethylester

Following the procedure described in Example 19 but starting from 4.2 g. (0.01 moles) of (+)-1α-[(2'-ethoxycarbonyl-2'-hydroxyimino)-ethyl]-1β-ethyl-1,2,3,4,6,7,12,12bβ-octahydro-indolo[2,3-a]quinolizine hydrochloride, 25.2 g. (60%) of the title compound are obtained, melting at 148° to 151° C.

$[\alpha_D^{20}] = -145.8°$ (c=1, CHCl$_3$).

What we claim is:

1. Racemic cis hydroximinooctahydroindole[2,3-a]quinolizines of the formula (II)

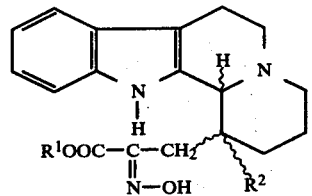

wherein R$^1$ and R$^2$ are identical or different alkyl groups having from one to 6 carbon atoms and pharmaceutically acceptable acid addition salts thereof.

2. Racemic trans hydroxyiminooctahydro[2,3-a]quinolizine derivatives of the formula (II)

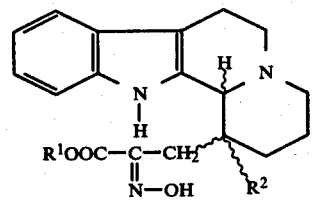

wherein R$^1$ and R$^2$ are identical or different alkyl groups having from one to 6 carbon atoms, and pharmaceutically acceptable acid addition salts thereof.

3. Optically active trans hydroxyiminooctahydroindolo[2,3-a]quinolizine derivatives of the formula (IIa)

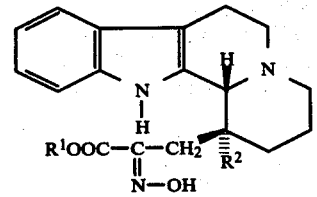

wherein R$^1$ and R$^2$ are identical or different alkyl groups having from one to 6 carbon atoms, and pharmaceutically acceptable acid addition salts thereof.

4. Optically active trans hydroxyiminooctahydroindolo[2,3-a]quinolizine derivatives of the formula (IIb)

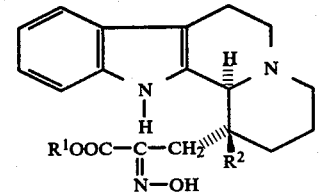

wherein R$^1$ and R$^2$ are identical or different alkyl groups having from one to 6 carbon atoms, and pharmaceutically acceptable acid addition salts thereof.

5. Optically active cis hydroxyiminooctahydroindolo[2,3-a]quinolizine derivatives of the formula (IIc)

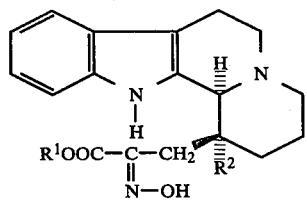

(IIc)

wherein $R^1$ and $R^2$ are identical or different alkyl groups having from one to 6 carbon atoms, and pharmaceutically acceptable acid addition salts thereof.

6. Optically active cis hydroxyiminooctahydroindolo[2,3-a]quinolizine derivatives of the formula (IId)

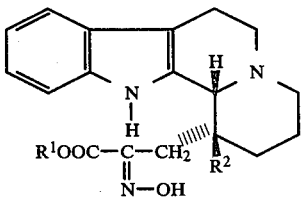

(IId)

wherein $R^1$ and $R^2$ are identical or different alkyl groups having from one to 6 carbon atoms, and pharmaceutically acceptable acid addition salts thereof.

* * * * *